(12) United States Patent
Rohde

(10) Patent No.: US 9,588,097 B2
(45) Date of Patent: Mar. 7, 2017

(54) METHOD AND APPARATUS FOR DETERMINING AN AGEING STATE OF A LUBRICANT

(71) Applicant: Siemens Aktiengesellschaft, München (DE)

(72) Inventor: Joachim Rohde, Aachen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 440 days.

(21) Appl. No.: 14/035,623

(22) Filed: Sep. 24, 2013

(65) Prior Publication Data

US 2014/0083172 A1    Mar. 27, 2014

(51) Int. Cl.
G01N 33/28 (2006.01)

(52) U.S. Cl.
CPC ..... G01N 33/2888 (2013.01); G01N 33/2858 (2013.01)

(58) Field of Classification Search
CPC ........... G01N 33/2858; G01N 33/2888; G01N 33/2835; G01N 33/30
USPC .............................. 73/53.05, 53.07
See application file for complete search history.

(56) References Cited

U.S. PATENT DOCUMENTS

| 7,581,434 B1* | 9/2009 | Discenzo | G01N 33/2888 |
| | | | 73/53.01 |
| 8,149,004 B2* | 4/2012 | Raju | G01N 17/02 |
| | | | 324/698 |
| 2002/0129644 A1* | 9/2002 | Petty | G01N 21/293 |
| | | | 73/61.46 |

FOREIGN PATENT DOCUMENTS

JP    S63-40855 A    2/1988

OTHER PUBLICATIONS

Mujahid Adnan et al; Monitoring automotive oil degradation; analytical tools and onboard sensing technologies; pp. 1197-1209; Analytical and Bioanalytical Chemistry; Springer Verlag, Berlin; ISSN: 1618-2650; DOI: 10.1007/S00216-012-6186-1; xp 035098922; 2012; DE; Jul. 1, 2012.
Ko Y. G. et al; Confirmation of heavy metal ions in used lubricating oil from a passenger car using chelating self-assembled monolayer; pp. 27-31; Journal of Colloid and Interface Science, Academic Press, New York; ISSN: 0021-9797; DOI: 10.1016/J.JCIS.2006.04.050; xp 024909256; 2006; US; Sep. 1, 2006.

* cited by examiner

*Primary Examiner* — Michael A Lyons
*Assistant Examiner* — Suman K Nath
(74) *Attorney, Agent, or Firm* — Henry M. Felereisen LLC.

(57) ABSTRACT

In a method for determining an ageing state of lubricant which comes into contact with a metallic surface in a machine to be lubricated, a metal ion content or a change over time of a metal ion content in the lubricant is determined. The metal ion content can be determined by a measuring sensor which is disposed in the machine or disposed in a lubricant line connected to the machine.

9 Claims, 3 Drawing Sheets

METHOD AND APPARATUS FOR DETERMINING AN AGEING STATE OF A LUBRICANT

CROSS-REFERENCES TO RELATED APPLICATIONS

This application claims the priority of European Patent Application, Serial No. 12185788.2, filed Sep. 25, 2012, pursuant to 35 U.S.C. 119(a)-(d), the disclosure of which is incorporated herein by reference in its entirety as if fully set forth herein.

BACKGROUND OF THE INVENTION

The present invention relates to a method and apparatus for determining an ageing state of a lubricant.

The following discussion of related art is provided to assist the reader in understanding the advantages of the invention, and is not to be construed as an admission that this related art is prior art to this invention.

The quality of lubricants in mechanical and plant engineering, especially in drive technology, is a significant influencing variable which determines the availability, the reliability and the safety of the entire drive train or of the lubricated components. Experience in the maintenance of transmission units shows that even the best lubricants age and have to be changed. In such cases there is an ever greater trend away from scheduled lubricant change intervals to state-dependent change periods.

Generally-applicable criteria as to when the quality of a lubricant becomes inadequate do not exist however. As a rule an individual limit value is to be observed for each application and each lubricant.

It would therefore be desirable and advantageous to address prior art shortcomings.

SUMMARY OF THE INVENTION

According to one aspect of the present invention, a method for determining an ageing state of lubricant which comes into contact with a metallic surface in a machine to be lubricated includes determining a metal ion content or a change over time of a metal ion content in the lubricant.

To ensure clarity, it is necessary to establish the definition of several important terms and expressions that will be used throughout this disclosure. The term "machine" generally relates to all moving machine parts in which lubricant is used for lubrication, e.g. gear units, especially gear wheels, and motors. The term "lubricant" may relate to a liquid lubricant, e.g. a lubricating oil, but also to a paste-like lubricant, e.g. a flow grease or lubricating grease.

The invention is based on the underlying recognition that an ageing lubricant forms aggressive components which can chemically attack a metallic surface, and that a release of metal ions caused by this from the metallic surface can be used as an indicator for an ageing state of a lubricant.

Since a majority of the components in lubricated machines consist as a rule of iron or steel respectively, the proof of iron ions in the lubricant is preferred. However other ions of other metals, e.g. copper or tin, can serve as proof of the ageing state of the lubricant. The type of metal of the ions can provide information about which components are being attacked by the lubricant. Iron ions can indicate an attack on gear wheels and roller bearings. Copper ions can indicate an attack on brass cages and brass or bronze bearings. Tin ions can indicate an attack on friction bearings made of white metal or bronze.

So long as lubricant is not attacking the metal surface no metal ions or relatively few metal ions are released from the surface. If metal ions are being released it must be checked whether this is the result of a desired or tolerated process, i.e. a reaction of an additive added to the lubricant or an undesired greatly accelerated removal of metal ions as a result of lubricant ageing.

The present invention makes it possible to reliably monitor the quality of a lubricant to be found in a machine. The advantage of the present method compared to known methods for determining lubricant ageing, such as a measurement of an acid value or an evaluation of an infrared spectrum lies above all in a simple definition of a limit value. A release of metal ions from a metallic surface only starts to accelerate when the aggressiveness of the lubricant increases. Definition of a limit value thus does not require any complex trials which only apply in each case specifically for individual combinations of application and lubricant. Instead of this a limit value can be defined for each lubricant by means of simple laboratory tests.

According to another advantageous feature of the present invention, the metal ion content can be determined by a measuring sensor which is disposed in the machine or is connected via a lubricant line to the machine. The lubricant state can be detected directly, during operation of the machine to be lubricated, with the aid of the sensor which detects metal ions.

According to another advantageous feature of the present invention, the metal ion content can be determined by taking a lubricant sample and analyzing the lubricant sample detection. The lubricant state can be tested by a chemical analysis of a lubricant sample in a laboratory.

A laboratory method based on detection reagents is a cation proof for iron ions in reagent glass using a detection reagent, namely the iron ion proof with thiocyanate, thioglycol acids or red or yellow potassium ferrocyanide. A subsequent quantitative determination can be undertaken by spectroscopy.

According to another aspect of the present invention, an apparatus for determining an ageing state of lubricant which comes into contact with a metallic surface in a machine to be lubricated includes a sensor configured for determining a metal ion content or a change over time to a metal ion content in the lubricant, a processor configured for evaluating a measured value obtained by the sensor, and a transmission unit configured for transmitting the measured value from the sensor to the processor.

The lubricant state can also be checked by a physical method for proof of metal ions.

According to another advantageous feature of the present invention, the sensor can include ion-selective electrodes for measuring a concentration of metal ions.

According to another advantageous feature of the present invention, the sensor can include a photometric analysis system for measuring metal ions. Such photometric analysis systems are used for example in a measurement of iron ions in water or in medical technology.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
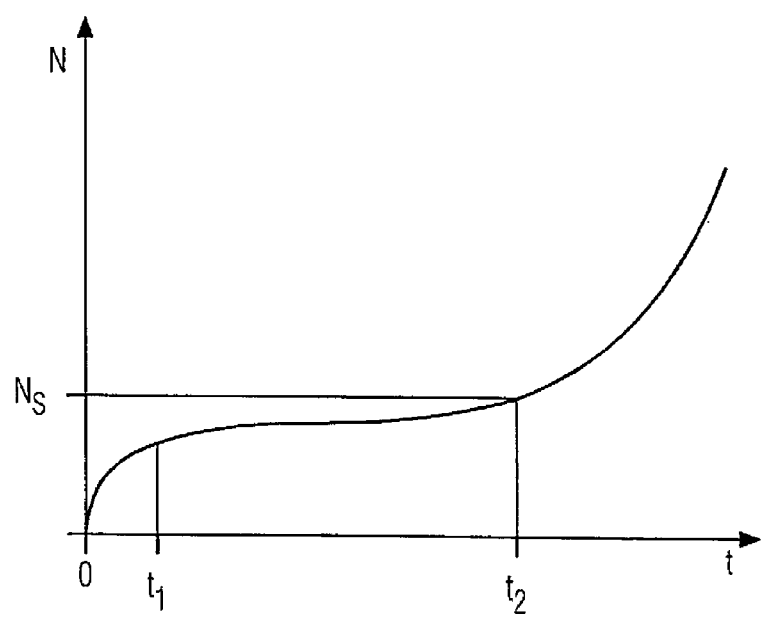
FIG. 1 shows a graph plotted over time of a number of metal ions in a lubricant.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a graph, in which a number of metal ions N in a lubricant which comes into contact with a metallic surface in a machine to be lubricated, is plotted over the time t. The time axis begins at point in time 0 at which the machine is commissioned. Up to a point in time t1 the number of metal ions N in the lubricant increases sharply, which is a result of the running-in of the machine, until the machine parts in contact with one another, e.g. gear wheels and shafts, have been "run in", there is relatively greater friction and thus a transfer of iron particles and also iron ions into the lubricant.

In a time interval between t1 and t2 the lubricant is still unconsumed so that it has a relatively small and only slightly increasing content of aggressive chemical compounds which release iron ions from the metallic surface of the machine to be lubricated. Therefore the number of metal ions N in the lubricant is relatively small in the time interval between t1 and t2.

At the point in time t2 the number of metal ions N in the lubricant amounts to $N_S$ (S=threshold value). From this point in time t2 onwards the number of metal ions N in the lubricant increases sharply. The reason for this is that the ageing lubricant forms a number of aggressive components which become increasingly larger, which can chemically attack a metallic surface. As a result of the growing aggressiveness of the lubricant an accelerated release of metal ions from a metallic surface takes place. The point in time t2 thus defines a point in time at which the lubricant is to be changed. This point in time t2, at which the number of metal ions N assumes the value $N_S$ in the lubricant, can be established in accordance with the present invention by determining the metal ion content N: When the metal ion content reaches the value $N_S$ the lubricant change time t2 is reached.

As an alternative a change to the metal ion content in the lubricant 6 can also be monitored. In this case the time interval between t=0 and t1 is omitted because the cause of the sharp rise occurring therein is not the ageing process of the lubricant but wear between metallic components in contact with one another, e.g. of two components of a gear wheel meshing with one another during the running-in phase of the machine. In the time interval between t1 and t2 the change over time dN/dt of the number of metal ions N in the lubricant is relatively slow. Only as from point in time t2 when the lubricant is already old, is a marked change of the number of metal ions N in the lubricant, namely a sharp increase, to be observed. This means that instead of an absolute number of metal ions in the lubricant, an additional change dN/dt of the number of metal ions in the lubricant can be used as a symptom for the ageing state of the lubricant.

Figure 2:
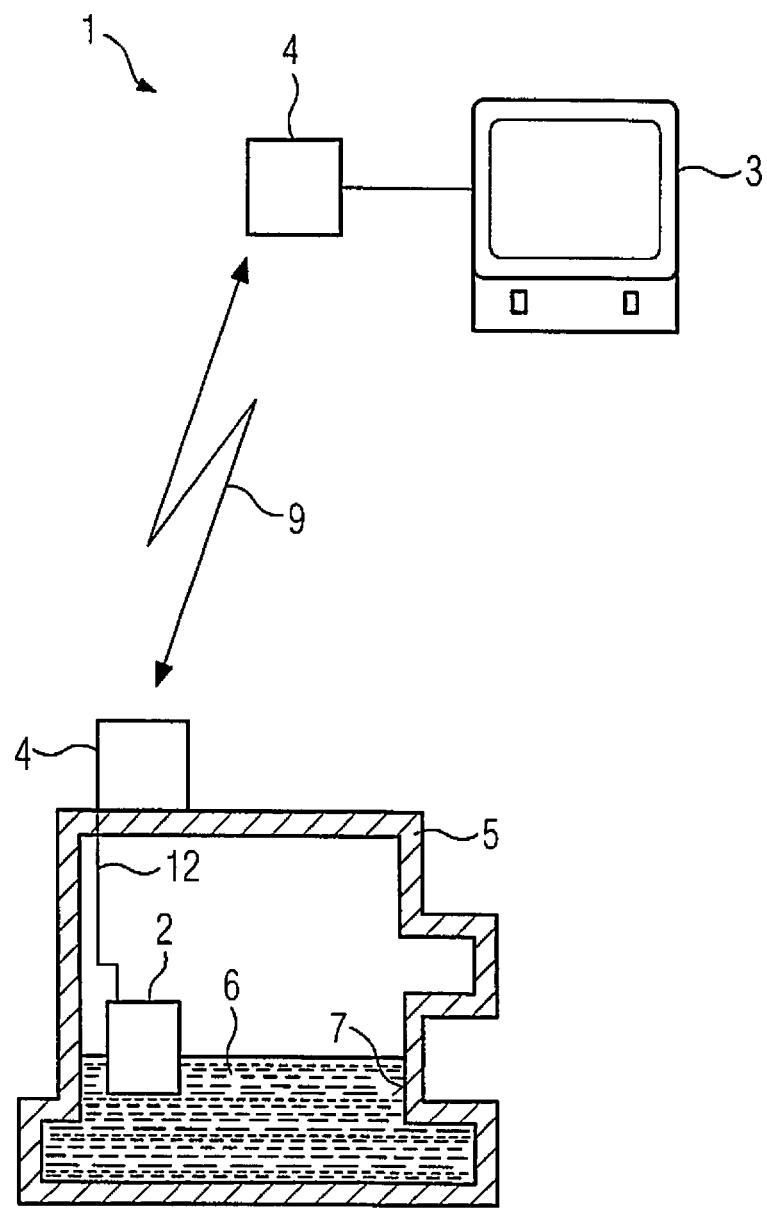
FIG. 2 shows a first exemplary embodiment of an apparatus for determining an ageing state of lubricant which comes into contact with a metallic surface in a machine to be lubricated.

FIG. 2 shows an apparatus 1 for carrying out a method for determining an ageing state of a lubricant 6 which comes into contact with a metallic surface 7 in a machine 5 to be lubricated.

Installed inside the machine 5 is a sensor 2 which serves to determine a metal ion content or a change to a metal ion content in the lubricant. The sensor is partly immersed in an oil sump filled with lubricant 6 and determines measured values which allow information to be provided about the concentration of metal ions in the lubricant. For example the sensor 2 includes ion-selective electrodes which are in contact with the lubricant.

The measured values obtained by the sensor 2 are transmitted via a data line 12 to a transmission unit 4 which performs a wireless transmission 9 of the measured values between a send unit and a corresponding receive unit. The measured values are finally transmitted by the receive unit to a processor 3 which performs an evaluation of the measured values obtained by the sensor 2. If the measured values reveal that the metal ion content lies above a threshold value $N_S$, the processor 3 generates a notification to an operator of the apparatus 1, e.g. as a warning message on a screen or as an e-mail.

Figure 3:
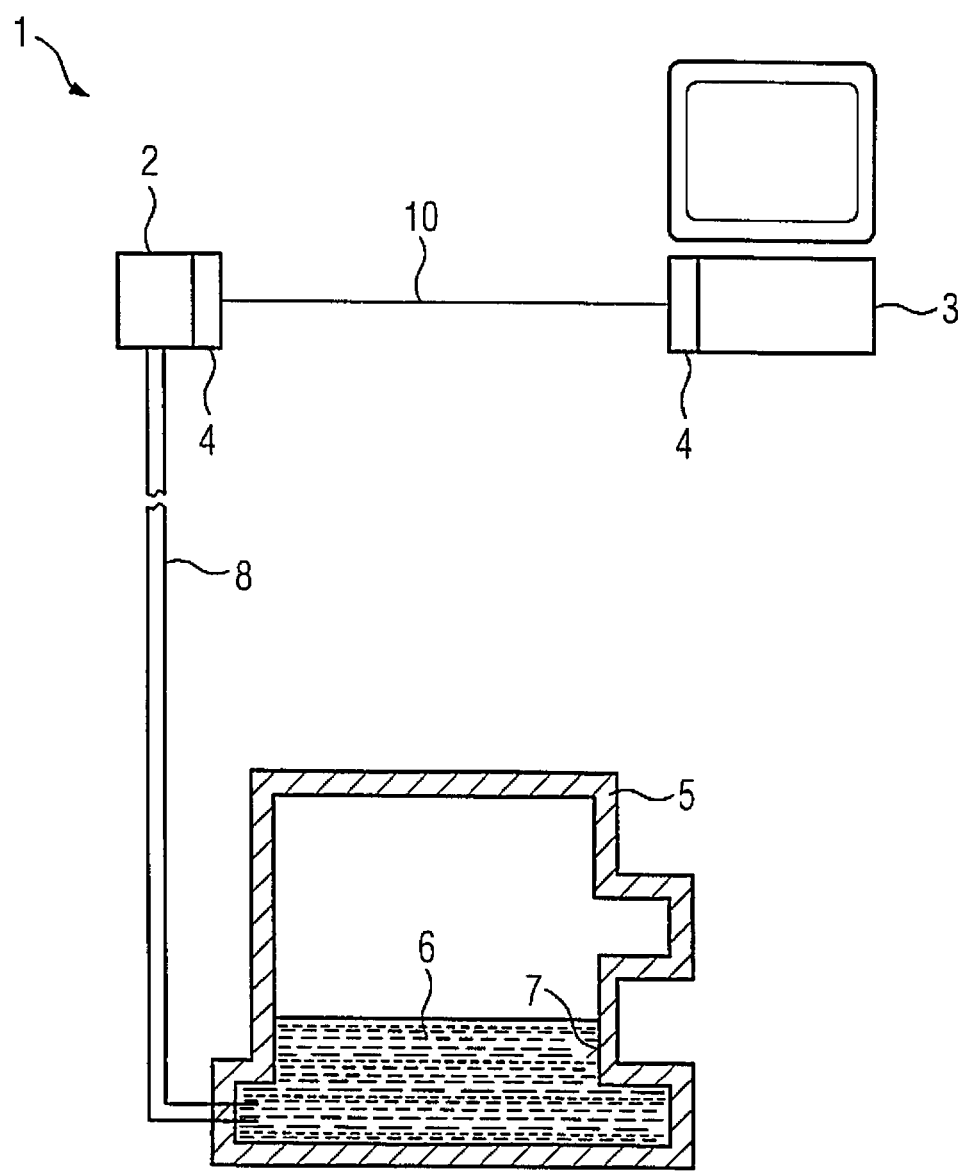
FIG. 3 shows a second exemplary embodiment of an apparatus for determining an ageing state of lubricant which comes into contact with a metallic surface in a machine to be lubricated.

FIG. 3 likewise shows an apparatus 1 for carrying out a method for determining an ageing state of a lubricant 6 which comes into contact with a metallic surface 7 in a machine 5 to be lubricated. In this case the sensor 2 which is used for determining a metal ion content or a change to a metal ion content in the lubricant, by contrast with the apparatus shown in FIG. 2, is not is disposed inside the machine 5 but instead outside the machine 5.

The external sensor 2 is connected via a lubricant line 8 to a lubricant collection container, e.g. an oil sump, of the machine 5. Lubricant 6 is supplied to the sensor from the machine 5 via the lubricant line 8. This corresponds to taking a lubricant sample. The lubricant line 8 is preferably embodied as a ring line, with a lubricant feed leading from the machine 5 to the sensor 2 and a lubricant return leading in the opposite direction. In this way "fresh" lubricant 6 can continuously be supplied to the sensor 2 from the machine 5, i.e. lubricant with a current metal ion content, as sample material.

The sensor 2 determines measured values on the basis of the supplied lubricant 6 which allow information to be provided about the concentration of metal ions in the lubricant 6. This corresponds to an analysis of the lubricant sample. For example the sensor 2 includes a photometric analysis system for measuring metal ions.

The measured values obtained by the sensor 2 are transmitted to a transmission unit 4 which via a data cable 10 carries out a transmission of the measured values between a send unit and a corresponding receive unit. The measured values are finally transmitted by the receive unit to a processor 3 which performs the evaluation of the measured values obtained by the sensor 2. If the measured values reveal that the metal ion content lies above a threshold value $N_S$, the processor 3 generates a notification to an operator of the apparatus 1, e.g. as a warning message on a screen or as an e-mail.

Although the invention has been illustrated and described in greater detail on the basis of the preferred exemplary embodiments, the invention is not limited by the disclosed examples and other variations can be derived herefrom by the person skilled in the art without departing from the scope of protection of the invention.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. A method for determining an ageing state of lubricant which comes into contact with a metallic surface in a machine to be lubricated, comprising determining a metal ion content or a change over time of a metal ion content in the lubricant as a result of chemically attacking the metallic surface by aggressive components of the lubricant which are formed when the lubricant ages, and using a resulting release of metal ions by the metallic surface as an indicator for an ageing state of the lubricant.

2. The method of claim 1, wherein the metal ion content is determined by a measuring sensor which is disposed in the machine.

3. The method of claim 1, wherein the metal ion content is determined by a measuring sensor which is disposed in a lubricant line connected to the machine.

4. The method of claim 1, wherein the metal ion content is determined by taking a lubricant sample and analyzing the lubricant sample.

5. The method of claim 1, further comprising comparing the determined metal ion content or determined change over time of the metal ion content with a reference value, and triggering a notification when the metal ion content or the change over time of the metal ion content exceeds the reference value.

6. An apparatus for determining an ageing state of lubricant which comes into contact with a metallic surface in a machine to be lubricated, comprising:
   a sensor configured for determining a metal ion content or a change over time to a metal ion content in the lubricant as a result of chemically attacking the metallic surface by aggressive components of the lubricant which are formed when the lubricant ages, and using a resulting release of metal ions by the metallic surface as an indicator for an ageing state of the lubricant;
   a processor configured for evaluating a measured value obtained by the sensor; and
   a transmission unit configured for transmitting the measured value from the sensor to the processor.

7. The apparatus of claim 6, wherein the sensor includes ion-selective electrodes.

8. The apparatus of claim 6, wherein the sensor includes a photometric analysis system.

9. A method, comprising:
   determining a measured value commensurate with a metal ion content or a change over time of a metal ion content in a lubricant which comes into contact with a metallic surface in a machine to be lubricated as a result of chemically attacking the metallic surface by aggressive components of the lubricant which are formed when the lubricant ages, and using a resulting release of metal ions by the metallic surface as an indicator for an ageing state of the lubricant;
   evaluating the measured value; and
   determining an ageing state of the lubricant in dependence on the evaluated measured value.

\* \* \* \* \*

UNITED STATES PATENT AND TRADEMARK OFFICE
CERTIFICATE OF CORRECTION

PATENT NO. : 9,588,097 B2  
APPLICATION NO. : 14/035623  
DATED : March 7, 2017  
INVENTOR(S) : Joachim Rohde Page 1 of 1

It is certified that error appears in the above-identified patent and that said Letters Patent is hereby corrected as shown below:

On the Title Page

Item [30], insert:  
--September 25, 2012    (EP) 12185788.2--.

Signed and Sealed this  
Thirteenth Day of March, 2018

Andrei Iancu  
*Director of the United States Patent and Trademark Office*